United States Patent [19]

Fehr et al.

[11] 4,091,099
[45] May 23, 1978

[54] 6-HYDROCARBON-ERGOPEPTINES

[75] Inventors: Theodor Fehr, Dornach; Paul Stadler, Biel-Benken, both of Switzerland

[73] Assignee: Sandoz Ltd., Basel, Switzerland

[21] Appl. No.: 645,568

[22] Filed: Dec. 31, 1975

[30] Foreign Application Priority Data

Jan. 6, 1975 Switzerland ............................ 68/75

[51] Int. Cl.$^2$ .................... C07D 519/02; A61K 31/48
[52] U.S. Cl. ...................................... 424/250; 544/346
[58] Field of Search ................. 260/268 PC, 268 PE; 424/250

[56] References Cited

U.S. PATENT DOCUMENTS

| | | | |
|---|---|---|---|
| 3,586,683 | 6/1971 | Stadler et al. | 260/268 PC |
| 3,652,569 | 3/1972 | Stadler et al. | 260/268 TR |
| 3,920,664 | 11/1975 | Clemens et al. | 260/268 PE |

FOREIGN PATENT DOCUMENTS 769,260   3/1957   United Kingdom.

OTHER PUBLICATIONS

Merck Index, 8th edition, p. 14, (1968).

*Primary Examiner*—Jose Tovar
*Attorney, Agent, or Firm*—Gerald D. Sharkin; Robert S. Honor; Thomas O. McGovern

[57] ABSTRACT

This invention provides new compounds of formula I,

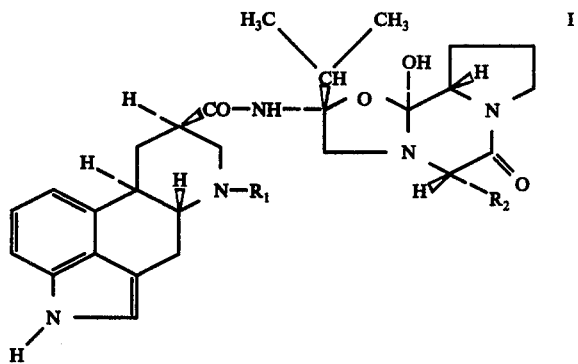

wherein
  $R_1$ is hydrogen, alkyl of 2 to 8 carbon atoms, or phenylalkyl of 7 to 9 carbon atoms, and
  $R_2$ is branched alkyl of 3 or 4 carbon atoms or benzyl,
useful as agents for the treatment of migraine, hypotonia and orthostatic disorders.

15 Claims, No Drawings

6-HYDROCARBON-ERGOPEPTINES

The present invention relates to 9,10-dihydro-ergopeptines

The present invention provides compounds of formula I,

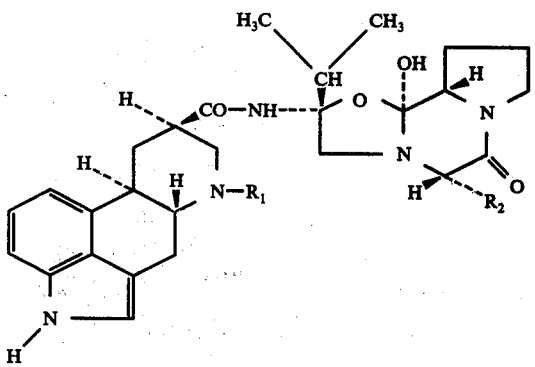

wherein
$R_1$ is hydrogen, alkyl of 2 to 8 carbon atoms, or phenylalkyl of 7 to 9 carbon atoms, and
$R_2$ is branched alkyl of 3 or 4 carbon atoms or benzyl.

The present invention provides a process for the production of a compound of formula I, as defined above, which comprises condensing a reactive functional derivative of an acid of formula II,

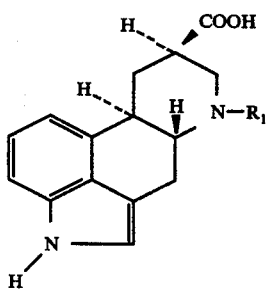

wherein $R_1$ is as defined above,
with a compound of formula III,

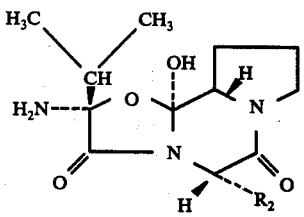

wherein $R_2$ is as defined above,
in acid addition salt form.

The process is a conventional condensation process for the production of peptide lysergic acid amides.

Reaction conditions are well known in ergot chemistry. Suitable reactive functional derivatives which can be used for the compounds of formula II are also known. The process may be effected in analogous manner to that described in Example 1.

As reactive functional derivatives may be used the acid chloride hydrochloride, the acid azide or a mixed anhydride of an acid of formula II with sulphuric acid or trifluoroacetic acid. Preferably the reactive functional derivative is a reaction product of an acid of formula II and an amide chloride produced by reacting a chlorinating agent and a N-di(lower)alkyl substituted acid amide of a lower aliphatic carboxylic acid.

As chlorinating agent may be used phosgene or oxalyl chloride. For the preparation of the amide chloride preferred amides are for example dimethyl formamide or dimethyl acetamide.

The compound of formula III is preferably used in the form of the hydrochloride.

Of the acids of formula II those wherein $R_1$ is hydrogen or straight chain alkyl of 2 to 6 carbon atoms are known [Die Mutterkornalkaloide (1964), page 67 (A. Hofmann)]. The remaining acids of formula II may be produced analogous to 6-nor-6-ethyl-9,10-dihydro-lysergic acid [see Helv. Chim. Acta 53, 2197 f (1970)].

The compounds of formula III are known [Helv. Chim. Acta 52, 1549 f (1969)].

$R_1$ is preferably alkyl of 2 to 4 carbon atoms, especially ethyl, n-propyl, iso-propyl, or iso-butyl.

$R_2$ is preferably iso-propyl or sec.-butyl.

The compounds of formula I are named herein based on the following moiety of formula IV,

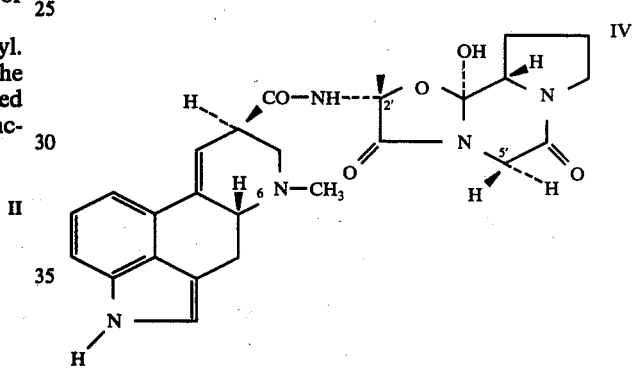

which is called ergopeptine.

Insofar as the production of any starting material is not particularly described these compounds are known, or may be produced and purified in accordance with known processes, or in a manner analogous to processes described herein, e.g. in the Examples, or to known processes.

Free base forms of compounds of formula I may be converted into acid addition salt forms in conventional manner and vice versa. Suitable acids for salt formation include hydrochloric acid.

In the following Examples all temperatures are in degrees Centigrade and are uncorrected.

EXAMPLE 1

6-nor-6-n-propyl-9,10-dihydro-2'β,5'α-diisopropyl-ergopeptine 8.6 cc (100 millimol) of oxalyl chloride dissolved in 20 cc of acetonitrile are added dropwise within 10 minutes to a solution of 300 cc of dimethyl formamide and 150 cc of acetonitrile at −10° to −15° and stirring is effected for 10 minutes. 29.8 g (100 millimol) of anhydrous 6-nor-6-isopropyl-9,10-dihydro-lysergic acid are added at −20°. The mixture is stirred for 30 minutes at −10°. Upon cooling to −20°, 200 cc of pyridine and 17.4 g (50 millimol) of (2R,5S,10aS,10bS)-2-amino-2,5-diisopropyl-3,6-dioxo-10b-hydroxy-octahydro-8H-oxazolo[3,2-a]pyrrolo[2,1-c]pyrazine hydrochloride are added and the mixture is stirred for 2 hours at 0°. Working up is effected by adding 100 cc of buffer solution of pH 4 and the reaction mixture is distributed between methylene chloride and 2N caustic soda solution. The organic phases are washed twice with water, dried over sodium sulphate and evaporated to dryness at the rotavapor. The resulting crude base is dried in a high vacuum, is dissolved in ethanol in order to crystallize and the solution was inoculated. The title compound is obtained having a M.P. of 180° (decomposition); $[\alpha]_D^{20} = -8.7°$ (c = 1.046 in methanol).

In a manner analogous to Example 1, the following compounds may be produced:

| Ex. No. | Compound of formula I | Starting materials | M.P. | $[\alpha]_D^{20}$ |
|---|---|---|---|---|
| 2 | 6-nor-6-ethyl-9,10-dihydro-2'β,5'α-diisopropyl-ergopeptine | 28.4 g 6-nor-6-ethyl-9,10-dihydro-lysergic acid and 17.4 g A* | 177–178° (decomp.) | −11.8° (c = 0.518 in CH$_3$OH) |
| 3 | 6-nor-6-isopropyl-9,10-dihydro-2'β,5'α-diisopropyl-ergopeptine | 29.8 g 6-nor-6-isopropyl-9,10-dihydro-lysergic acid and 17.4 g A* | 221° (decomp.) | −30.1° (c = 0.466 in CH$_3$OH) |
| 4 | 6-nor-6-n-butyl-9,10-dihydro-2'β,5'α-diisopropyl-ergopeptine | 31.2 g 6-nor-6-n-butyl-9,10-dihydro-lysergic acid and 17.4 g A* | 170–171° (decomp.) | −10.7° (c = 1.025 in CH$_3$OH) |
| 5 | 6-nor-6-isobutyl-9,10-dihydro-2'β,5'α-diisopropyl-ergopeptine | 31.2 g 6-nor-6-isobutyl-9,10-dihydro-lysergic acid and 17.4 g A* | 191° (decomp.) | −22.0° (c = 1.005 in CH$_3$OH) |
| 6 | 6-nor-6-isopentyl-9,10-dihydro-2'β,5'α-diisopropyl-ergopeptine | 32.6 g 6-nor-6-isopentyl-9,10-dihydro-lysergic acid and 17.4 g A | 164–166° (decomp.) | −14.2° (c = 1.032 in CH$_3$OH) |
| 7 | 6-nor-6-n-hexyl-9,10-dihydro-2'β,5'α-diisopropyl-ergopeptine | 34.0 g 6-nor-6-n-hexyl-9,10-dihydro-lysergic acid and 17.4 g A* | 216° (decomp.) (c = 1.043 | −15.2° in CH$_3$OH) |
| 8 | 6-nor-6-phenethyl-9,10-dihydro-2'β,5'α-diisopropyl-ergopeptine | 36.9 g 6-nor-6-phenethyl-9,10-dihydro-lysergic acid and 17.4 g A* | 210° (decomp.) | −6.4° (c = 0.740 in CH$_3$OH |
| 9 | 6-nor-6-isopropyl-9,10-dihydro-2'β-isopropyl-5'α-sec.butyl-ergopeptine | 29.8 g 6-nor-6-isopropyl-9,10-dihydro-lysergic acid and 18.1 g B** | 211° (decomp.) | −9.1° (c = 0.811 in CH$_3$OH) |
| 10 | 6-nor-6-n-butyl-9,10-dihydro-2'β-isopropyl-5'α-sec.-butyl-ergopeptine | 31.2 g 6-nor-6-butyl-9,10-dihydro-lysergic acid and 18.1 g B** | 186–187° (decomp.) | −8.7° (c = 1.0 in CH$_2$Cl$_2$) |
| 11 | 6-nor-6-isopentyl-9,10-dihydro-2'β-isopropyl-5'α-sec.butyl-ergopeptine | 32.6 g 6-nor-6-isopentyl-9,10-dihydro-lysergic acid and 18.1 g B** | 221° (decomp.) | −10.9° (c = 1.048 in CH$_2$Cl$_2$) |
| 12 | 6-nor-9,10-dihydro-2'β-isopropyl-5'α-benzyl-ergopentine | 25.6 g 6-nor-9,10-dihydro-lysergic acid and 19.8 g C*** | 192° (decomp.) | +9.2° (c = 0.978 in dimethylsulphoxide) |
| 13 | 6-nor-6-isobutyl-9,10-dihydro-2'β-isopropyl-5-'α-benzyl ergopeptine | 31.2 g 6-nor-6-isobutyl-9,10-dihydro-lysergic acid and 19.8 g C*** | 198–199° (decomp.) | −0 34.3° (c = 0.968 in CH$_2$Cl$_2$) |

*A = (2R,5S,10aS,10bS)-2-amino-2,5-di-isopropyl-3,6-dioxo-10b-hydroxy-octahydro-8H-oxazolo[3,2-a] pyrrolo[2,1-c]pyrazine-hydrochloride
**B = (2R,5S,10aS,10bS)-2-amino-2-iso-propyl-5-sec.-butyl-3,6-dioxo-10b-hydroxy-octahydro-8H-oxazolo-[3,2-a]pyrrolo[2,1-c]pyrazine-hydrochloride
***C = (2R,5S,10aS,10bS)-2-amino-2-iso-propyl-5-benzyl-3,6-dioxo-10b-hydroxy-octahydro-8H-oxazolo[3,2-a]pyrrolo[2,1-c]pyrazine-hydrochloride The compounds of formula I have not been described in the literature.

The compounds of formula I are useful because they possess pharmacological activity in animals. In particular, the compounds of formula I are useful as hypertonic agents, as indicated by standard tests.

For example a pressor effect is observed in the spinal cat preparation on administration i.v. of from about 0.001 to about 1 mg/kg animal body weight of the compounds. Additionally, a blocking effect on the α-adrenergic receptors in the isolated seminal vesicle of the guinea pig using concentrations of from about $1 \times 10^{-9}$ to about $1 \times 10^{-6}$ g/ml of the compounds. Furthermore an increase in the peripheral vascular resistance is observed in the autoperfused cat calf muscle (Mellander Cat preparation) on administration i.a. of from about 5 to about 60 μg/kg muscle of the compounds.

Furthermore the compounds of formula I are useful as agents for the treatment and prophylaxis of migraine, as indicated by standard tests. For example a serotonin antagonism is observed in the isolated rat uterus test using concentrations of from about 0.5 to about 15 mg/liter of the compounds.

Furthermore, the compounds of formula I are useful as agents for the treatment of orthostatic disorders, as indicated by the pressor effect in the above-mentioned test. Additionally, this indication is confirmed by a tonisation of the capacity vessels in the above-mentioned cat test.

For all the above mentioned use the dosage will, of course, vary depending on the compound employed, mode of administration and therapy desired. However, in general, satisfactory results are obtained when administered at a daily dosage of from 0.001 mg to about 2 mg per kg animal body weight, conveniently given in divided doses 2 to 4 times a day or in sustained release form. For the larger mammal, the total daily dosage is in the range from about 1 to about 100 mg, and dosage forms suitable for oral administration comprise from about 0.2 mg to about 50 mg of the compounds admixed with a solid or liquid pharmaceutical carrier or diluent.

In an Example a suitable dose range for all animals is from ca. 0.01 to ca. 0.5 mg/kg. For the larger mammal a suitable daily dose is from ca. 1.5 mg to 30 mg preferably administered in daily doses of from about 0.75 to 10 mg.

The Example 1 compound is the most interesting compound.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be formulated so as to be, for example, a solution or a tablet.

Further acids for acid addition salt formation include methane-sulphonic acid, fumaric acid, hydrobromic acid, malic acid.

We claim:

1. A compound of formula I,

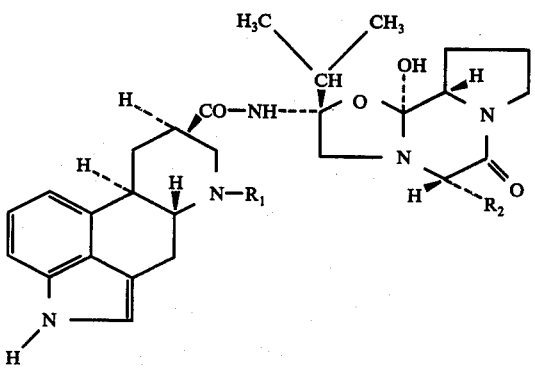

wherein

R₁ is isopropyl, isobutyl, isopentyl or phenethyl, and
R₂ is branched alkyl of 3 or 4 carbon atoms or benzyl,
in free base form or in pharmaceutically acceptable acid addition salt form.

2. A compound of claim 1, wherein R₂ is isopropyl, iso- or sec.-butyl or benzyl.

3. A compound of claim 1, wherein R₂ is isopropyl or sec.-butyl.

4. A pharmaceutical composition for use in the treatment of hypotonia, orthostatic disorders or migraine comprising an effective amount of a compound of claim 1 in association with a pharmaceutical carrier or diluent.

5. A method of treating hypotonia, orthostatic disorders or migraine in an animal in need of said treatment comprising administering a therapeutically effective amount of a compound of claim 1.

6. The compound according to claim 1 which is 6-nor-6-isopropyl-9,10-dihydro-2′β, 5′α-diisopropyl-ergopeptine.

7. The compound according to claim 1 which is 6-nor-6-isobutyl-9,10-dihydro-2′β, 5′α-diisopropyl-ergopeptine.

8. The compound according to claim 1 which is 6-nor-6-isopentyl-9,10-dihydro-2′β, 5′β-diisopropyl-ergopeptine.

9. The compound according to claim 1 which is 6-nor-6-phenethyl-9,10-dihydro-2′β, 5′α-diisopropyl-ergopeptine.

10. The compound according to claim 1 which is 6-nor-6-isopropyl-9,10-dihydro-2′β-isopropyl-5′α-sec. butyl-ergopeptine.

11. The compound according to claim 1 which is 6-nor-6-isopentyl-9,10-dihydro-2′β-isopropyl-5′α-sec. butyl-ergopeptine.

12. The compound according to claim 1 which is 6-nor-6-isobutyl-9,10-dihydro-2′β-isopropyl-5′α-benzyl ergopeptine.

13. A pharmaceutical composition according to claim 4, comprising 0.2 to 50 milligrams per unit dosage.

14. A method according to claim 5 in which 1 to 100 milligrams of the compound are administered daily.

15. A method according to claim 14 in which 0.2 to 50 milligrams of the compound are administered per unit dosage.

* * * * *